United States Patent
Rosen

(10) Patent No.: US 11,510,760 B2
(45) Date of Patent: Nov. 29, 2022

(54) HYDRATING CANCELLUS BONE CORTICAL DRILL

(71) Applicant: Dan Rosen, Sherman Oaks, CA (US)

(72) Inventor: Dan Rosen, Sherman Oaks, CA (US)

(*) Notice: Subject to any disclaimer, the term of this patent is extended or adjusted under 35 U.S.C. 154(b) by 338 days.

(21) Appl. No.: 16/572,709

(22) Filed: Sep. 17, 2019

(65) Prior Publication Data

US 2021/0077230 A1 Mar. 18, 2021

(51) Int. Cl.
*A61C 8/00* (2006.01)
*A61C 3/02* (2006.01)
*A61C 17/02* (2006.01)
*A61B 17/16* (2006.01)

(52) U.S. Cl.
CPC ............ *A61C 8/0089* (2013.01); *A61C 3/02* (2013.01); *A61C 17/02* (2013.01); *A61B 17/1673* (2013.01); *A61B 2217/007* (2013.01)

(58) Field of Classification Search
CPC ..... A61C 8/0089; A61C 3/02; A61B 17/1673; A61B 2217/007; A61B 17/885; A61B 2017/1651; A61B 2017/1653; B23B 27/10
See application file for complete search history.

(56) References Cited

U.S. PATENT DOCUMENTS

| | | | | |
|---|---|---|---|---|
| 2,411,209 A * | 11/1946 | Furth | ........................ | F28G 3/14 407/56 |
| 5,259,398 A * | 11/1993 | Vrespa | ................. | A61B 17/863 128/898 |
| 5,655,907 A * | 8/1997 | Landgraf | ................. | A61C 3/02 433/165 |
| 6,171,312 B1 * | 1/2001 | Beaty | ................. | A61B 17/1604 606/80 |
| 2006/0111724 A1 * | 5/2006 | Yeung Wai Ping | . | A61C 8/0089 606/80 |
| 2015/0158132 A1 * | 6/2015 | Kopton | .................... | B23C 3/124 29/557 |
| 2015/0230893 A1 * | 8/2015 | Huwais | .............. | A61B 17/1604 433/173 |
| 2015/0306685 A1 * | 10/2015 | Rakes | ...................... | B24D 5/10 407/11 |
| 2016/0015483 A1 * | 1/2016 | Kumar | ................. | A61C 8/0068 606/301 |
| 2019/0151958 A1 * | 5/2019 | Hammond, Jr. | ..... | B23D 77/006 |

FOREIGN PATENT DOCUMENTS

EP 1488745 * 12/2004 ............. A61B 17/16

* cited by examiner

*Primary Examiner* — Heidi M Eide
(74) *Attorney, Agent, or Firm* — John Alumit

(57) ABSTRACT

A cortical drill for hydrating and drilling cancellous bone when preparing a dental implant includes a stem portion and a drill portion, the stem portion with a locking notch and a water inlet configured for receiving fluid under pressure into the cortical drill. The drill portion has an elongated substantially conical body having an outer wall. The drill portion has a slot portion, and the slot portion includes a cut-out forming an inlet along a peripheral surface of the conical body. A plurality of jets are formed in the slot portion, with the jets in communication with the water inlet, and the jets arranged along the slot portion, such that fluid travelling under pressure into the water inlet, travels through the stem portion and the drill portion, and exits the jets in the slot portion.

11 Claims, 3 Drawing Sheets

HYDRATING CANCELLUS BONE CORTICAL DRILL

BACKGROUND

Field of the Invention

The present invention generally relates to dentistry. More specifically, the present invention relates to a hydrating cancellous bone cortical drill for use in installing dental implants.

Related Art

Cortical drills are known in the art. Typically, dental implants are anchored in the cancellous bone, which lies beneath a layer of cortical bone. In implant procedures, a cortical drill is employed to create a space in the cortical bone. One feature characteristic of cortical drills is the lack of a cutting edge, thus relying largely on pressure to create a space for the drill in a cortical bone matrix.

In the process of drilling cortical bone using a cortical drill, water is employed. Namely, the cavity is periodically flushed with water to assist in enlarging the cavity. Currently the process of introducing water into a cortical bone cavity involves introducing a cortical drill into a patient's cortical bone, and periodically removing the cortical drill to flush the site with water. There are several problems with such a procedure.

First, water is a key component in enlarging a cortical bone site, and by introducing water alternatively with the cortical bone screw causes the procedure to be less effective and take longer. Second, even in instances where the water supply can be deployed while a cortical drill is in use, the water is not brought to bear directly against the cancellous bone at the drill site. This also causes the procedure to be less effective.

Hence, what is needed is a cortical drill that provides water under pressure directly against cortical bone matrix at a drill site without the limitations of existing techniques.

SUMMARY

A cortical drill for hydrating and drilling cancellous bone when preparing a dental implant includes a stem portion and a drill portion. The stem portion includes a locking notch and a water inlet configured for receiving fluid under pressure into the cortical drill. The drill portion includes an elongated substantially conical body having an outer wall, the drill portion arranged in linear parallel with the stem portion. The drill portion also includes a top portion and a tip portion arranged distally from the top. The drill portion has a slot portion, and the slot portion includes a cut-out forming an inlet along a peripheral surface of the conical body.

A plurality of jets in the cut-out form an inlet. The jets are in communication with the water inlet, and the jets are arranged along the slot portion, such that fluid travelling under pressure into the water inlet, travels through the stem portion and the drill portion, and exits the jets in the slot portion.

In various alternative embodiments, the slot portion may have an aggressively angled surface opposite a convex surface for increasing water pressure when turning. The top of the drill portion may be flattened adjacent the stem portion, and the drill portion may have an increasing slope along the outer wall, which terminates at a tip portion which is distal from the stem portion. In other embodiments, the slot portion extends from the top portion to the tip portion.

In yet other alternative embodiments, the slot portion is deepest near the top portion and shallowest near the tip portion. Alternatively, the slot portion may be cylindrical, having a uniform diameter from the top portion to the tip portion. The slot portion preferably comprises a left opening edge and a right opening edge framing a slot opening. The left opening edge and the right opening edge are preferably in peripheral contour such that the drill portion has no cutting edge. Additionally, the jets may be angled downward toward the tip portion such that fluid expelled from the jets travels in a generally downward direction, and the cortical drill is preferably one of a plurality of differently sized cortical drills having substantially the same features, together comprising a cortical drill kit.

The invention may also be characterized as a cortical drill for hydrating and drilling cancellous bone when preparing a dental implant, with the drill including a stem portion and a drill portion. The stem portion includes a locking notch and water inlet configured for receiving fluid under pressure, and the drill portion includes an elongated substantially conical body with an outer wall, the drill portion is arranged in linear parallel with the stem portion, with an increasing slope along the outer wall, terminating at a tip portion distal from the stem portion.

The drill portion includes a top portion with the tip portion arranged distally from the top portion, with an increasing slope along the outer wall, terminating at the tip portion; the drill portion further comprising a slot portion extending from the top portion to the tip portion, the slot portion comprising a cut-out forming an inlet along a peripheral surface of the conical body. A plurality of jets are positioned in the cut-out which forms an inlet, the jets are in communication with the water inlet, and are arranged along the slot portion, such that fluid travelling under pressure into the water inlet travels through the stem portion and the drill portion, and exits the jets in the slot portion.

When characterized in this manner, the top of the drill portion may be flattened adjacent the stem portion. The slot portion may be deepest near the top portion and shallowest near the tip portion. Alternatively, the slot portion may be cylindrical, having a uniform diameter from the top portion to the tip portion. Preferably, the slot portion includes a left side opening edge and a right side opening edge framing a slot opening. The left side opening edge and the right side opening edge are preferably in peripheral contour such that the drill portion has no cutting edge. Additionally, the jets are preferably angled downward toward the tip portion such that fluid expelled from the jets travels in a generally downward direction, and the cortical drill may be one of a plurality of differently sized cortical drills having substantially the same features, together forming a cortical drill kit.

Finally, the apparatus may be characterized as a cortical drill for hydrating and drilling cancellous bone when preparing a dental implant, with the drill having a stem portion and a drill portion. The stem portion has a locking notch and a water inlet configured for receiving fluid under pressure. The drill portion comprising an elongated substantially conical body with an outer wall, the drill portion arranged in linear parallel with the stem portion with an increasing slope along the outer wall, and terminating at a tip portion distal from the stem portion.

The drill portion includes a top portion and the tip portion arranged distally from the top portion, with an increasing slope along the outer wall, terminating at the tip portion. The drill portion also has a slot portion extending from the top portion to the tip portion, the slot portion comprising a cut-out forming an inlet along a peripheral surface of the conical body and the slot portion being deepest near the top portion and shallowest near the tip portion. The slot portion also has a left opening edge and a right opening edge framing a slot opening. The left opening edge and the right opening edge being in peripheral contour such that the drill portion has no cutting edge.

A plurality of jets are positioned in the slot portion, with the jets being in communication with the water inlet. The jets are arranged along the slot portion, such that fluid travelling under pressure into the water inlet travels through the stem portion and the drill portion, and exits the jets in the slot portion. The cortical drill is preferably only one of a plurality of differently sized cortical drills having substantially the same features in a cortical drill kit.

Figure 1:
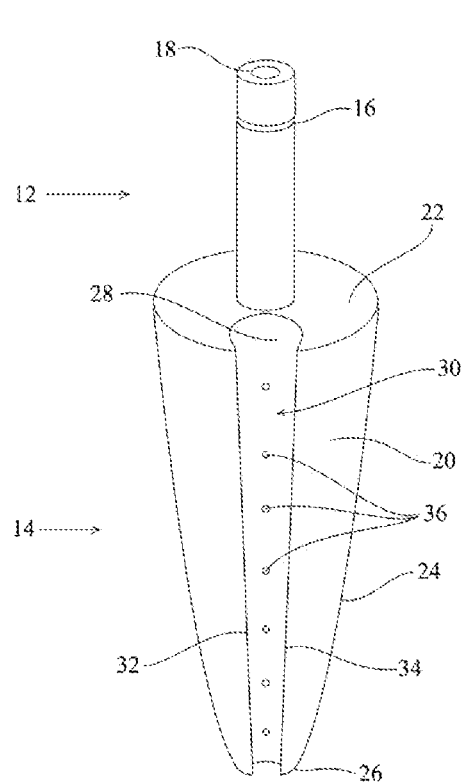
FIG. 1 illustrates a perspective view of a hydrating cancellous bone cortical drill.

REFERENCE NUMBERS 10. hydrating cancellous bone cortical drill
12. stem portion
14. drill portion
16. locking notch
18. water inlet
20. conical body
22. top portion
24. outer wall
26. tip portion
28. slot
30. opening
32. left opening edge
34. right opening edge
36. jets
38. water conduit
40. alternative slot portion
100. first alternative cortical drill
128. first alternative slot portion
200. second alternative cortical drill
228. second alternative slot portion
300. third alternative cortical drill
328. third alternative slot portion
400. fourth alternative cortical drill
428. fourth alternative slot portion
500. fifth alternative cortical drill
528. fifth alternative slot portion

DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

Referring to FIG. 1, a preferred embodiment hydrating cancellous bone cortical drill 10 includes a stem portion 12 and a drill portion 14. The stem portion 12 is similar to a conventional cortical drill attachment, preferably including a locking notch 16 and a water inlet 18 for receiving water (or any other suitable fluid) under pressure. The drill portion 14 is characterized by an elongated, substantially conical body 20 arranged in linear parallel along the axis of the stem portion 12. In the illustrated embodiment, the drill portion 14 includes a substantially flattened top portion 22, with a generally increasing slope along an outer wall 24, and terminating at a tip portion 26.

Still referring to FIG. 1, the conical body 20 is characterized by a slot portion 28 forming an inlet along the peripheral surface of the conical body, in axial parallel to the stem portion 12. The slot portion 28 preferably extends along the entire length of the conical body 20, but in various alternative embodiments, it may extend only partially along the conical body 20. Preferably, the slot portion 28 is deepest near the top portion 22 of the drill portion 14 and shallowest near the tip portion 26, but in various alternative embodiments, the slot portion 28 may be cylindrical, and having the same diameter the entire length of the drill portion 14. In the illustrated embodiment, the slot portion 28 is formed as a columnar cut out of the conical body 20 to create a relatively deep chamber with a circular circumference wider than an opening 30 framed by a left opening edge 32 and a right opening edge 34. In other embodiments, the slot may be formed in a more shallow configuration, such that the slot portion 28 is merely an indentation with no left opening edge 32 or right opening edge 34, according to preference.

Still referring to FIG. 1, the slot portion 28 of the conical body 20 is further characterized by a series of openings, or jets 36 in fluid communication with the water inlet 18. Preferably, a plurality of jets 36 are provided, although any number of jets 36 are contemplated according to preference, including considerations based on the size of the slot portion 28 and conical body 20. When the cortical drill 10 is in use, water travels under pressure from a dental instrument (not shown) into the water inlet 18, and through the conical body 20, to exit the jets 36 under pressure. Pressurized water from the jets 36 assists travel of the cortical drill 10 through a matrix of cancellous bone, including gently moving the matrix aside, to prepare room for an implant, and flushing out any loose material in the process.

Figure 2:
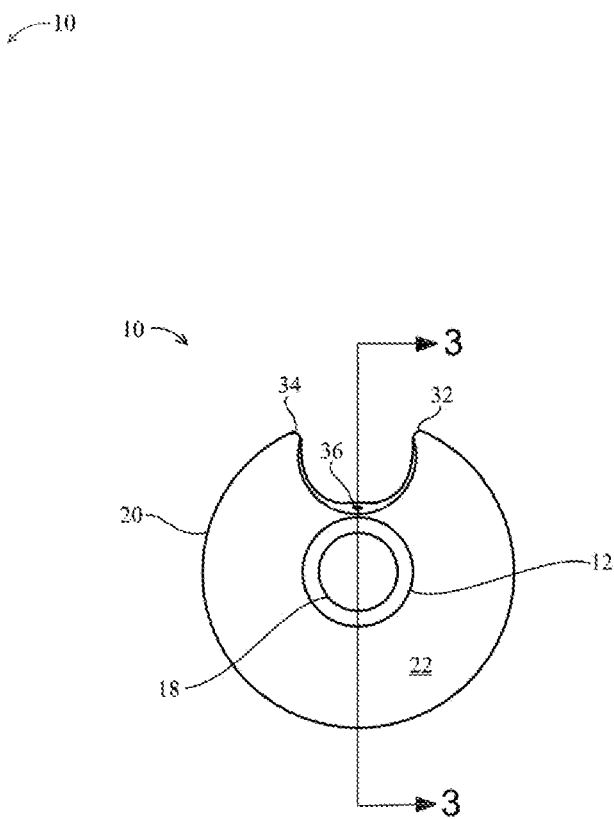
FIG. 2 illustrates a top view of the cortical drill.

Referring to FIG. 2 a top view of the cortical drill 10 is shown. The slot portion 28 is shown penetrating deep into the conical body 20, in the process forming the left opening edge 32 and the right opening edge 34 (reversed in this view, when the cortical drill 10 of FIG. 1 is rotated into a top view). Although a single jet 36 is shown in FIG. 2 for reference, this structure is intended to represent any number of a series of jets 36 extending along the slot portion 28. As shown in FIG. 2, the conical body 20 does not present any substantial cutting edge, since the left opening edge 32 and the right opening edge 34 are in peripheral contour with the conical body 20. In an alternative embodiment, to help prevent any cutting by the left opening edge 32 or the right opening edge 34, the one of them that is trailing relative to the direction of turn, may be formed inward of the leading one, thereby ensuring that neither the left opening edge 32 or the right opening edge 34 catch on any of the cancellous bone matrix as the cortical drill 10 extends therethrough.

Figure 3:
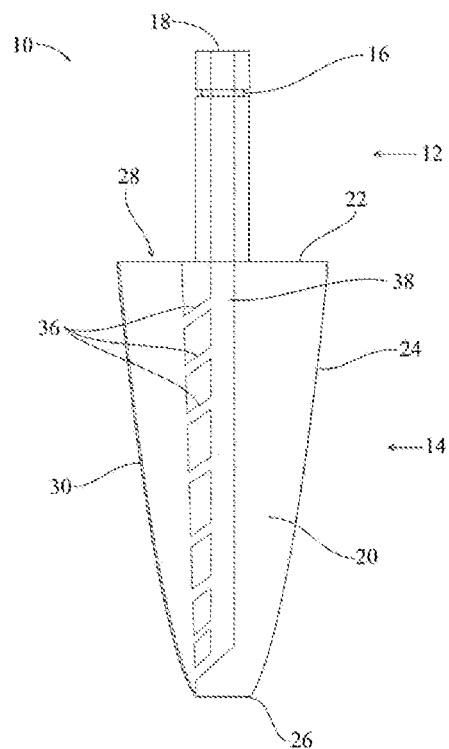
FIG. 3 illustrates a section elevation view of the drill.

Referring to FIG. 3, a cut-away elevation view of the cortical drill 10 is shown. In this view a water conduit 38 is shown connecting the water inlet 18 to the jets 36 that lead into the slot portion 28. In the illustrated embodiment, the jets 36 are angled downward (i.e. toward the tip portion 26. This causes water from the water inlet 18 to be expelled in a generally downward direction, maximizing the water pressure toward the tip portion 26, and thus maximizing the pressure of the water against the bone matrix as the cortical drill 10 spins, even as water is expelled upward through the slot portion 28 and out the top portion 22 of the conical body 20.

Figure 4:
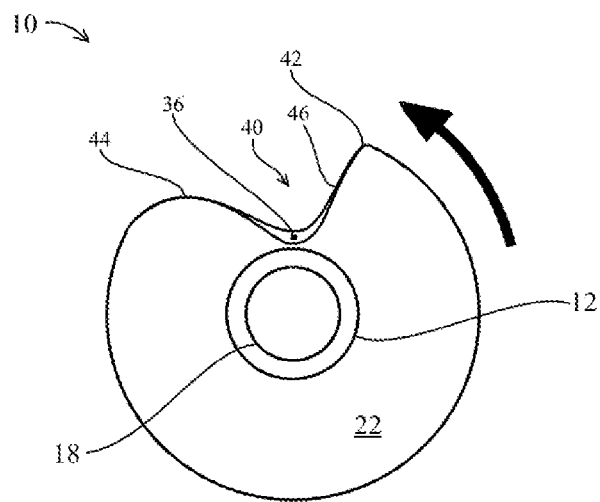
FIG. 4 illustrates a top view of an alternative embodiment of the cortical drill.

Referring to FIG. 4, the cortical drill 10 is shown having an alternative slot portion 40 characterized by a single opening edge 42. Opposite the single opening edge 42 is a convex surface 44, such that the alternative slot portion 40 occupies substantially as great an area as the primary embodiment slot portion 28 (FIGS. 1-3). This configuration, allows the alternative slot portion 40 to have an aggressively angled surface 46 opposite the convex surface 44. Thus, when the cortical drill 10 is rotated in the direction of arrow 48, the aggressively angled surface 46 helps to increase the pressure of the water exiting the jets 36. By increasing the water pressure in this manner, increased widening of cancellous bone at the drilling site can be achieved. While the illustrated embodiment shows the aggressively angled surface 46 on the left side of the alternative slot portion 40 when viewed from above, it should be understood that a reversed configuration with the aggressively angled surface 46 arranged to the right of the convex surface 44 is also possible according to drill direction.

Figure 5:
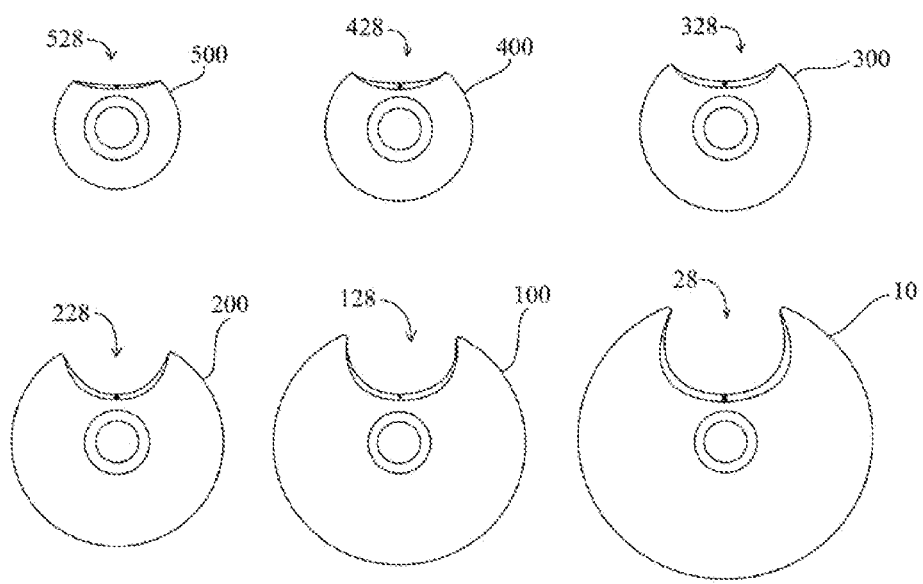
FIG. 5 illustrates a set of hydrating cancellous bone cortical drills having a variety of diameters.

Referring to FIG. 5, it is anticipated that the cortical drill 10 shown in FIGS. 1-3 will be part of a cortical drill set of varying sizes. In the illustrated embodiment, the large cortical drill 10 would be included with a series of consecutively smaller cortical drills 100, 200, 300, 400, 500, with substantially the same features. As shown in the illustrated embodiment, due to size considerations, in particular the circumference of the smaller cortical drills 100, 200, 300, 400, 500, as the circumference decreases, each of the slot portions 28, 128, 228, 328, 428, 528, may become less pronounced. In other embodiments, the slot portions may remain configured as an almost fully enclosed space as shown in FIGS. 1-3. Additionally, the slot portions may be configured similar to the alternative slot portion 40 of FIG. 4, and the size of the alternative slot portion 40 configured to correspond to the size of the smaller cortical drills 100, 200, 300, 400, 500.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A cortical drill for hydrating and drilling cancellous bone when preparing a dental implant, to prepare room for the dental implant, the drill comprising:
    a stem portion and a drill portion;
    the stem portion comprising a locking notch and a water inlet configured for receiving fluid under pressure;
    the drill portion comprising an elongated conical body having an outer wall, the drill portion arranged in linear parallel with the stem portion;
    the drill portion comprising a top portion and a tip portion arranged distally from the top;
    the drill portion further comprising a non-helical slot portion, the slot portion comprising a straight elongated cut-out along a peripheral surface of the conical body;
    the non-helical slot portion further comprising a non-cutting leading edge and a non-cutting trailing edge; and
    a plurality of jets in the slot portion formed by the cut-out, the jets being in communication with the water inlet, and the jets arranged along the slot portion, such fluid travelling under pressure into the water inlet, travels through the stem portion and the drill portion, and exits the jets in the slot portion under sufficient pressure to assist in displacing the cancellous bone,
    wherein the slot portion comprises an angled surface opposite a convex surface, for increasing water pressure against the angled surface.

2. The cortical drill of claim 1 wherein the drill portion comprises an increasing slope along the outer wall, terminating at the tip portion distal from the stem portion.

3. The cortical drill of claim 1 wherein the slot portion extends from the top portion to the tip portion.

4. The cortical drill of claim 1 wherein the slot portion is deepest near the top portion and shallowest near the tip portion.

5. The cortical drill of claim 1 wherein the slot portion comprises a left opening edge and a right opening edge framing a slot opening.

6. The cortical drill of claim 1 wherein the jets are angled downward toward the tip portion such that fluid expelled from the jets travels in a generally downward direction.

7. A cortical drill for hydrating and drilling cancellous bone when preparing a dental implant, to prepare room for the dental implant, the drill comprising:
    a stem portion and a drill portion;
    the stem portion comprising a locking notch and water inlet configured for receiving fluid under pressure;
    the drill portion comprising an elongated conical body with an outer wall, the drill portion arranged in linear parallel with the stem portion with an increasing slope along the outer wall, terminating at a tip portion distal from the stem portion;
    the drill portion comprising a top portion and the tip portion is arranged distally from the top portion;
    the drill portion further comprising a non-helical slot portion extending from the top portion to the tip portion, the slot portion comprising a straight elongated cut-out along a peripheral surface of the conical body;
    the non-helical slot portion further comprising a non-cutting leading edge and a non-cutting trailing edge; and
    a plurality of jets in the cut-out, the jets in communication with the water inlet, and the jets arranged along the slot portion, such that fluid travelling under pressure into the water inlet, travels through the stem portion and the drill portion, and exits the jets in the slot portion under sufficient pressure to assist in displacing the cancellous bone,
    wherein the slot portion comprises an angled surface opposite a convex surface, for increasing water pressure against the angled surface.

8. The cortical drill of claim 7 wherein the top of the drill portion is flattened adjacent the stem portion.

9. The cortical drill of claim 7 wherein the slot portion is deepest near the top portion and shallowest near the tip portion.

10. The cortical drill of claim 7 wherein the slot portion comprises a left side opening edge and a right side opening edge framing a slot opening.

11. The cortical drill of claim 7 wherein the jets are angled downward toward the tip portion such that fluid expelled from the jets travels in a generally downward direction.

\* \* \* \* \*